United States Patent [19]

Helsley et al.

[11] Patent Number: 4,954,511

[45] Date of Patent: Sep. 4, 1990

[54] 4-PENTAFLUOROPHENOXYPIPERIDINES

[75] Inventors: Grover C. Helsley, Pluckemin; Larry Davis, Sergeantsville; Gordon E. Olsen, Somerset, all of N.J.

[73] Assignee: Hoechst-Roussell Pharmaceuticals Inc., Somerville, N.J.

[21] Appl. No.: 456,720

[22] Filed: Jan. 24, 1990

Related U.S. Application Data

[62] Division of Ser. No. 167,941, Mar. 14, 1988, Pat. No. 4,914,204.

[51] Int. Cl.$^5$ .................. A61K 31/445; C07D 211/94
[52] U.S. Cl. ..................................... 514/327; 514/252; 514/253; 544/360; 544/364; 546/215; 546/217; 546/31
[58] Field of Search .................... 546/215, 217, 24; 514/327

[56] References Cited

U.S. PATENT DOCUMENTS

| | | | |
|---|---|---|---|
| 3,542,794 | 11/1970 | Helsley | 546/217 |
| 3,853,384 | 8/1979 | Helsley et al. | 514/255 |
| 4,333,942 | 6/1982 | Klaus et al. | 546/216 |
| 4,458,075 | 7/1984 | Davis et al. | 546/198 |
| 4,914,204 | 4/1990 | Helsley et al. | 544/360 |

FOREIGN PATENT DOCUMENTS

| | | |
|---|---|---|
| 23706 | 11/1981 | European Pat. Off. . |
| 1964515 | 7/1970 | Fed. Rep. of Germany . |
| 2060619 | 5/1981 | United Kingdom . |

OTHER PUBLICATIONS

Filler et al., Biomedicinal Aspects of Fluorine Chemistry, pp. 2, 34–35 and 78.
Boswell et al., J. Med. Chem., vol. 17, No. 9, pp. 1000–1008, (1974).
Helsley et al., J. Med. Chem., vol. 21, No. 3, pp. 309–312, (1978).
Derwent Abstract, 12127d/08, EP 23706, 2/11/81.

*Primary Examiner*—Cecilia Shen
*Attorney, Agent, or Firm*—Elliott Korsen

[57] ABSTRACT

4-Phenafluorophenoxypiperidines and methods for alleviating pain and treating depression, convulsions, and hypertension utilizing compounds or compositions thereof are disclosed.

41 Claims, No Drawings

4-PENTAFLUOROPHENOXYPIPERIDINES

This is a division of application Ser. No. 167,941 filed 3/14/88, now U.S. Pat. No. 4,914,204.

This invention relates to 4-pentafluorophenoxypiperidines of the formula:

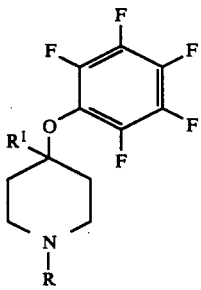

FORMULA I wherein $R^1$ is hydrogen or aryl; and R is a monovalent radical selected from the group consisting of hydrogen, cyano, loweralkyl, arylloweralkyl, bis-arylloweralkyl, aminoloweralkyl, (loweralkylamino)loweralkyl, (diloweralkylamino)loweralkyl, (diloweralkylphosphinyl)loweralkyl, heteroarylloweralkyl, and a group of the formula

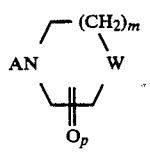

wherein A is loweralkylene, loweralkenylene or loweralkynylene, m is an integer having a value of zero or 1, W is $CH_2$ or $NR^{1a}$ wherein $R^{1a}$ is hydrogen, loweralkyl or aryl, and p is an integer having a value of zero or 1; which compounds, alone or in combination with one or more pharmaceutically acceptable carriers, are useful for alleviating pain, treating depression, reducing blood pressure, and treating convulsions.

Throughout the specification and appended claims a given formula or name shall encompass the stereo, optical, and geometrical isomers thereof, as well as the pharmaceutically acceptable acid addition salts and solvates (e.g., hydrates) of same.

Subgeneric to the 4-aryl-4-aryloxypiperidines of this invention are Formula I compounds wherein:
(a) R is hydrogen;
(b) R is loweralkyl;
(c) R is arylloweralkyl or bis-arylloweralkyl;
(d) R is aminoloweralkyl, (loweralkylamino)loweralkyl or (diloweralkylamino)loweralkyl;
(e) R is heteroarylloweralkyl;
(f) R is (diloweralkylphosphinyl)loweralkyl;
(g) R is a group of the formula:

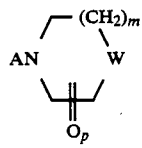

wherein A is loweralkylene, loweralkenylene, or loweralkynylene; m is an integer having a value of zero or 1; W is $CH_2$ or $NR^{1a}$ wherein $R^{1a}$ is hydrogen, loweralkyl or aryl, and p is an integer having a value of zero or 1;
(h) R is a group of the formula:

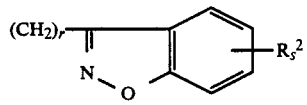

wherein r is an integer having a value of 2 or 3, s is an integer having a value from zero to 2 inclusive, and $R^2$ is halogen, loweralkyl or loweralkoxy;
(i) R is a group of the formula:

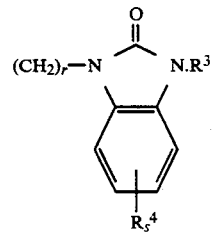

wherein r is an integer having a value of 2 or 3; s is an integer having a value of zero or 1; $R^3$ is hydrogen or loweralkyl; and $R^4$ is halogen or loweralkyl;
(j) R is

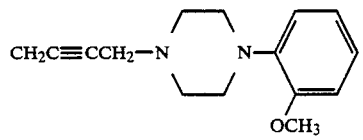

(k) R is

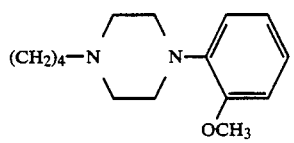

(l) R is cyano;
(m) $R^1$ is hydrogen;
(n) $R^1$ is aryl; and
(o) $R^1$ is an aryl radical of the formula

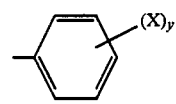

wherein X is halogen, loweralkyl, loweralkoxy or trifluoromethyl and y is an integer having a value of zero or 1.

As used throughout the specification and appended claims, the term "loweralkyl" shall mean a straight or branched chain hydrocarbon radical containing no unsaturation and having the formula $-C_xH_{2x+1}$ wherein x is an integer having a value of 1 to 7, inclusive, such as methyl, ethyl, 1-propyl, 2-propyl, 1-butyl, 1-pentyl, 2-pentyl, 3-hexyl, 4-heptyl, and the like; the term "loweralkoxy" shall mean an acyclic organic radical of the formula —$OC_xH_{2x+1}$ wherein x is an integer having a value of 1 to 7, inclusive, such as methoxy, ethoxy, 1-and 2-propoxy, 1,2-dimethylethoxy, 1-butoxy, 1- and 2-pentoxy, 3-hexoxy, 4-heptoxy and the like; the term "halogen" shall mean a member of the group consisting of fluorine, chlorine, bromine, and iodine radicals; the term "aryl" shall mean a phenyl group optionally substituted by one or more substitutents selected from the group consisting of halogen, loweralkyl, loweralkoxy, and trifluoromethyl; the term "arylloweralkyl" shall mean a loweralkyl group having an aryl substituent thereon; the term "heteroaryl" shall mean an aromatic heterocyclic mono- or dicyclic radical such as, for example, benzisoxazolyl, indolyl, benzimidazolyl, and the like, optionally substituted by one or more substitutents selected from the group consisting of halogen, loweralkyl, loweralkoxy, and oxo; the term "heteroarylloweralkyl" shall mean a loweralkyl group having a heteroaryl substituent thereon; the term "amino" shall mean a group of the formula —$NH_2$; the term "loweralkylamino" shall mean an amino group substituted at the nitrogen atom thereof by a loweralkyl group; the term "arylloweralkylamino" shall mean an amino group substituted at the nitrogen atom thereof by an arylloweralkyl group; the term "diloweralkylphosphinyl" shall mean a group of the formula

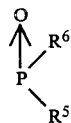

wherein $R^5$ and $R^6$ are loweralkyl; and the term "(diloweralkylphosphinyl)loweralkyl" shall mean a loweralkyl group having a diloweralkylphosphinyl substituent thereon.

The 4-pentafluorophenoxypiperidines of this invention are synthesized by the processes illustrated in the Reaction Schemes which follow.

As illustrated in Reaction Scheme A, Formula I compounds wherein R is hydrogen are produced by reacting 1-benzyl-4-hydroxypiperidine 1a with pentafluorophenol 2a to produce 1-benzyl-4-(2,3,4,5,6-pentafluorophenoxy)piperidine 3a which in turn is converted to 4-(2,3,4,5,6-pentafluorophenoxy)piperidine 4a from which a variety of 1-substituted derivatives 5a may be produced.

The reaction of 1-benzyl-4-hydroxypiperidine 1a with pentafluorophenol 2a is conducted in the presence of triphenylphosphine and diethylazodicarboxylate. Desirably, triphenylphosphine and diethylazodicarboxylate are utilized in quantities slightly in excess of stoichiometric amounts; the use of about a 10% excess of triphenylphosphine and diethylazodicarboxylate being preferred. The reaction is generally conducted in a non-reactive organic solvent at a temperature of from about 5° C. to about 50° C. preferably from about 20° C. to about 30° C. Suitable solvents include aromatic hydrocarbons such as, for example, benzene, xylene, toluene, and the like; benzene being preferred.

Removal of the benzyl protecting group of the 1-benzyl-4-(2,3,4,5,6-pentafluorophenoxy)piperidine 3a to afford the 4-(2,3,4,5,6-pentafluorophenoxy)piperidine 4a is generally achieved by catalytic reduction. Reaction with hydrogen in the presence of an appropriate catalyst (e.g. palladium, platinum, and the like; 10% palladium on carbon being preferred) at a pressure of from about 10 psi to about 60 psi, preferably from about 40 psi to about 50 psi, and a temperature of from about 5° C. to about 50° C., preferably from about 20° C. to about 30° C., is suggested as a convenient means of deprotection.

Substitution at the 1-position of the 4-(2,3,4,5,6-pentafluorophenoxy)piperidine 4a may be accomplished by any of numerous methods known in the art.

To provide Formula I compounds wherein R is a methyl group, the 4-(2,3,4,5,6-pentafluorophenoxy)piperidine 4a can be treated with formaldehyde in the presence of a suitable reducing agent (e.g. sodium borohydride). The reaction is typically carried out in an alkanol (e.g. methanol, ethanol, 1-and 2-propanol, and the like, methanol being preferred) or aqueous medium at a temperature of from about 0° C. to about 80° C., preferably from about 20° C. to about 30° C.

To synthesize a Formula I compound wherein R is a radical selected from the group consisting of loweralkyl, arylloweralkyl, bis-(aryl)loweralkyl, aminoloweralkyl, (loweralkylamino)loweralkyl, (diloweralkylamino)loweralkyl, diloweralkylphosphinylloweralkyl or heteroarylloweralkyl, a 4-(2,3,4,5,6-pentafluorophenoxy)piperidine 4a is reacted with a halide of the desired substituent R (preferably the chloride or fluoride) in a suitable organic solvent (e.g. halocarbons or polar aprotic solvents such as methylene chloride, dichloroethane, dichloromethane, chloroform, hexamethylphosphoramide, dimethylacetamide, dimethylformamide, dimethylsulfoxide, and the like: dimethylformamide being preferred). The reaction is generally conducted at a temperature of from about 20° C. to about 80° C., optimal reaction temperatures are however, subject to variation depending upon the particular solvent employed. The reaction is generally carried out in the presence of an acid acceptor (e.g. tertiary amines, alkali metal carbonates and bicarbonates, and the like, such as, for example, triethylamine, potassium carbonate, sodium carbonate, sodium bicarbonate, and the like). If desired, a promotor such as, for example, potassium iodide, may also be employed.

Substitution of certain substituents of the formula

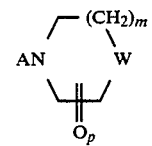

as previously defined is achieved by a variety of mechanisms tailored to the particular functional group R. For example, a formula I compound wherein R is

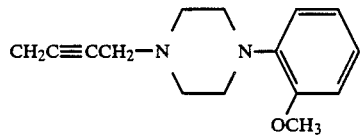

is produced by the reaction of 4-(2,3,4,5,6-pentafluorophenoxy)-1-propynyl piperidine with 4-(2-methoxyphenyl)piperazine and paraformaldehyde. The reaction is generally conducted in a non-reactive organic solvent (e.g. etheral solvents such as diethyl ether, tetrahydrofuran, dioxane, and the like; p-dioxane being preferred)

at a temperature of from about 5° C. to about 100° C., preferably from about 50° C. to about 80° C. If desired, the reaction is conducted in the presence of a suitable promoter (e.g. copper (I) chloride)

Reaction Scheme B illustrates the synthesis of the 4-aryl-4-(2,3,4,5,6-pentfluorophenoxy)piperidines of this invention. As illustrated, an anion of a 4-aryl-4-hydroxypiperidine 1b is reacted with hexafluorobenzene 2b to yield a 4-aryl-4-(2,3,4,5,6-pentafluorophenoxy)piperidine 3b from which a variety of 1-substituted derivatives 4b may be produced.

To generate the anion of the starting alcohol 1b, the alcohol is reacted with an alkali metal hydride (e.g. lithium hydride, potassium hydride, sodium hydride, and the like; sodium hydride being preferred) or a suitable organolithim compound (e.g. butyllithium or phenyllithium) at a temperature of from about 0° C. to about 100° C., preferably from about 10° C. to about 80° C., in an appropriate organic solvent. Suitable solvents include dipolar aprotic solvents such as hexamethylphosphoramide, dimethylsulfoxide, dimethylformamide, and the like; dimethylformamide being preferred. The resulting anion is thereafter reacted with hexafluorobenzene at a temperature of from about 0° C. to about 50° C., preferably from about 10° C. to about 25° C., in the solvent medium previously described.

As further illustrated by Reaction Scheme B, a cyano-substituted derivative 5b can be produced via the corresponding benzyl-substituted derivative 4b. The reaction of the 4-aryl-4-benzyl-4-(2,3,4,5,6-pentafluorophenoxy)piperidine 4b with a cyanogen halide (e.g. cyanogen bromide or chloride) is generally conducted in the presence of an acid acceptor (e.g. alkali metal carbonates and bicarbonates) in a halogenated hydrocarbon solvent (preferably chloroform) at a temperature of from about 5° C. to the reflux temperature of the solvent medium, reflux temperatures being preferred.

Substitution of the 4-aryl-4-(2,3,4,5,6-pentafluorophenoxy)piperidine 3b is as previously described in the context of 4-(2,3,4,5,6-pentafluorophenoxy)piperidine 4a.

Alternatively, the 1-substituted 4-aryl-4-(2,3,4,5,6-pentafluorophenoxy)piperidines of this invention can be produced by the reaction of an anion of a 1-substituted 4-aryl-4-hydroxypiperidine 1b with hexafluorobenzene 2b under conditions as previously described.

The compounds of this invention are useful as analgesic agents due to their ability to alleviate pain in mammals. The procedure employed to determine analgetic utility is a modification of the phenyl-p-benzoquinone writhing assay in mice, a standard assay for analgesia [Proc. Soc. Exptl. Bio. Med., 95, 729 (1957)]. Pursuant to the modified procedure phenyl-p-benzoquinone (Eastman, 12.5 mg) is dissolved in 5 ml of 95% ethanol and the solution is diluted to a total volume of 100 ml with distilled water. The solution is administered to the subject mice intraperitoneally at a dose of 10 ml per kg of body weight. A characteristic "writhe" an inward rotation of one or more feet with twisting and turning of the trunk, drawing in of the abdominal wall, lordosis and arching of the back, is produced.

Included among the compounds of this invention are the following:

1-ethyl-4-(2,3,4,5,6-pentafluorophenoxy)piperidine;
4-(pentafluorophenoxy)-1-[2-(N-methylamino)ethyl]-4-phenylpip eridine;
1-cyano-4-(2,3,4,5,6-pentafluorophenoxy)piperidine;
1-(2-aminoethyl)-4-(2,3,4,5,6-pentafluorophenoxy)-piperidine;
1-[2-(N-methylamino)ethyl]-4-(2,3,4,5,6-pentafluorophenoxypiperidine;
1-[4,4-bis-(4-fluorophenyl)butyl]-4-(2,3,4,5,6-pentafluorophenoxy)-4-phenylpiperidine;
1-(2-aminoethyl)-4-(4-fluorophenyl)-4-(2,3,4,5,6-pentafluorophenoxy)piperidine;
1-[2(N,N-dimethylamino)ethyl]-4-(2,3,4,5,6-pentafluorophenoxy)-4-phenylpiperidine;
1-[(dimethylphosphinyl)methyl]-4-(2-fluorophenyl)-4-(2,3,4,5,6-pentafluorophenoxy)piperidine;
1-{4-[1-[4-(2-methoxyphenyl)piperazin-1-yl]-2-butynyl]}-4-(2,3,4,5,6-pentafluorophenoxy)-4-phenylpiperidine; and
1-[(6-fluoro-1,2-benzisoxazol-3-yl)propyl]-4-(2,3,4,5,6-pentafluorophenoxy)-4-phenylpiperidine.

A total of 28 male mice (Charles River, CD-1), weighing 18 to 30 grams, are employed for a time response. The subject animals receive food and water ad libitum. Test compounds are dissolved in distilled water, or suspended in distilled water containing one drop of a suitable surfactant, such as Tween-80.

Four groups of five animals (20 animals) are given the test compound subcutaneously (s.c.) or orally (p.o.) at 15, 30, 45 and 60 minutes prior to administration of the phenyl-p-quinone. A control group (2 animals per group) receive an equal volume of the vehicle. After the administration of the phenyl-p-quinone, the mice are placed separately in one liter beakers, and after five minutes, are observed for ten minutes.

REACTION SCHEME A

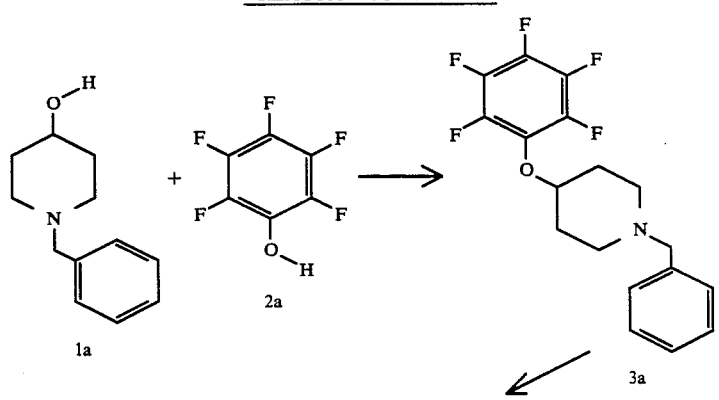

REACTION SCHEME A

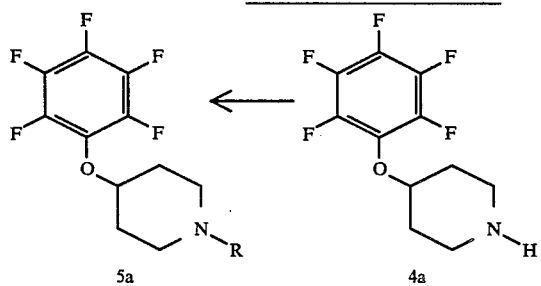

Wherein R is as herein defined

Wherein R is as herein defined

REACTION SCHEME B

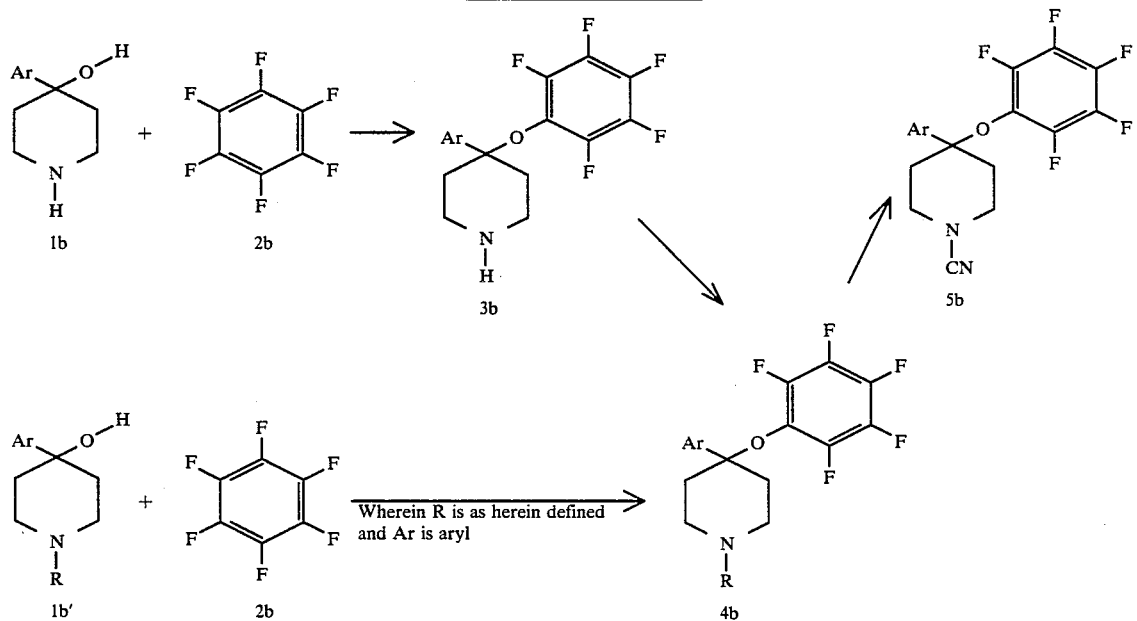

Wherein R is as herein defined and Ar is aryl

The number of writhes of each animal is recorded. The following is used to compute the percent inhibition:

$$\frac{\bar{x} \text{ Writhes in Control Group} - \bar{x} \text{ Writhes in Drug Group}}{\bar{x} \text{ Writhes in Control Group}} \times 100$$

The time period with the greatest percent of inhibition is considered the peak time. The results of the phenyl-p-quinone writhing assay for several of the compounds of this invention is provided in Table 1.

TABLE 1

| Compound | Analgesic Activity % Inhibition of writhing at a screening dose of 20 mg/kg, s.c. |
|---|---|
| 4-(2,3,4,5,6-pentafluorophenoxy)-piperidine hydrochloride | 20[1] |
| 1-{4-[4-(2-methoxyphenyl)-piperazin-1-yl)butyl]}-4-(2,3,4,5,6-pentafluorophenoxy)-piperidine dioxalate | 19[1] |
| 4-(4-chlorophenyl)-4-(2,3,4,5,6-pentafluorophenoxy)piperidine fumarate | 66 |
| 4-(4-fluorophenyl)-1-methyl-4-(2,3,4,5,6-pentafluorophenoxy)-piperidine hydrochloride | 49 |

TABLE 1-continued

| Compound | Analgesic Activity % Inhibition of writhing at a screening dose of 20 mg/kg, s.c. |
|---|---|
| 2,3,4,5,6-pentafluorophenoxy)-piperidine hydrochloride | 53 |
| 4-(4-methoxyphenyl)-1-methyl-4-(2,3,4,5,6-pentafluorophenoxy)-piperidine hydrochloride | 58 |
| 4-(4-fluorophenyl)-4-(2,3,4,5,6-pentafluorphenoxy)-piperidine hydrochloride | 56 |
| 4-4-methylphenyl)-4-(2,3,4,5,6-pentafluorophenoxy)-piperidine maleate | 52 |
| 1-cyano-4-(2,3,4,5,6-pentafluorophenoxy)-4-phenyl piperidine | |
| pentazocine | 1.3[1] |

[1]Reported as ED$_{50}$ values (i.e. the calculated dose at which the test compound effect a 50% inhibition of writhing).

Analgesia production is achieved when the compounds of this invention are administered to a subject requiring such treatment as an effective oral, parenteral or intravenous dose of from 0.1 to 50 mg/kg of body weight per day.

The compounds of this invention are also useful as anticonvulsants due to their anticonvulsant activity in mammals. Anticonvulsant activity is measured in male mice using the metrazol lethality assay (MTZ) described in *J. Pharmacol. Exp. Ther.*, 81, 402 (1944).

Groups of male mice (Charles River, CD-1), weighing 18 to 30 grams are employed in the Metrazol lethality assay. Test compounds are dissolved in distilled water or if insoluble, suspended in water, to which a surfactant, such as Tween-80 is added. The test compounds are administered orally, the administered dose being dissolved or suspended in 10 ml of solution or suspension per kg of animal body weight. Control animals (2 mice/group) receive water or water and Tween-80, i.e., the vehicle for administration of the test compound. Metrazol (pentylenetetrazol) is dissolved in water (concentration 225 mg of Metrazol/10 ml of solution), and the solution is administered subcutaneously to groups of five animals each at one or more time intervals of 15, 30, 60, 90, or 120 minutes after administration of the test compound. The number of animal alive 15 minutes after treatment with Metrazol is determined and recorded. The following formula is employed to calculate the percent protection against Metrazol lethality.

$$\% \text{ protection} = \frac{\text{number of surviving mice}}{\text{number of treated mice}} \times 100$$

A dose range determination is performed by substantially the same procedure as the time response determination. In the dose range determination, five groups of 10 animals per group are employed. This determination is generally reserved for those compounds which protect against lethality by greater than 70% at the screening dose employed. Linear regression analysis is used to estimate $ED_{50}$ values (i.e. the calculated dose at which the test compound effects a 50% inhibition of Metrazol lethality) and 95% confidence limits.

The anticonvulsant activity of several of the compounds of this invention as per the MTZ assay procedure is provided in Table 2.

TABLE 2

| Compound | Anticonvulsant Activity $ED_{50}$, mg/kg p.o. |
|---|---|
| 4-(4-fluorophenyl)-1-methyl-4-(2,3,4,5,6-pentafluorophenoxy)-piperidine hydrochloride | 80%[2] |
| 1-cyano-4-(2,3,4,5,6-pentafluorophenoxy)-4-phenyl piperidine | 55.2 |
| phenobarbital | 16.9 |

[2] Percent inhibition of Metrazol lethality at 30 mg/kg i.p.

Anticonvulsant activity is achieved when the compounds of this invention are administered to a subject requiring such treatment at an effective oral, parental or intravenous dose of from 1 to 100 mg/kg of body weight per day.

The compounds of this invention are also useful as antihypertensive agents due to their ability to depress blood pressure in mammals. Antihypertensive activity is measured in the spontaneous hypertensive rat by the indirect tail cuff method described in "Methods in Pharmacology", A. Schwartz, Ed., Vol. I, Appleton-Century Crofts, New York, N.Y., 1971, p. 135. In this procedure a group of five animals is treated orally for three days with the test compound in relation to a control group of the same number. The drop in blood pressure is measured on the third day following administration. The antihypertensive activities of representative compounds, expressed as a decrease in mean arterial blood pressure (in mm Hg), are given in Table 3 along with the activity of a standard compound.

TABLE 3

| | SHR |
|---|---|
| Compound | mm dec. in blood pressure at 50 mg/kg p.o. |
| 1-[-(6-fluoro-1,2-benzisoxazol-3-yl)propyl]-4-(2,3,4,5,6-pentafluorophenoxy)-piperidine hydrochloride | 62 |
| 1-benzyl-4-(2,3,4,5,6-pentafluorophenoxy)-4-phenylpiperidine | 40 |
| guanethidine | 20 |

Antihypertensive activity is achieved when the compounds of this invention are administered to a subject requiring such treatment at an effective oral, parental or intravenous dose of from 1 to 100 mg/kg of body weight per day.

The compounds of this invention are also useful as antidepressants by virtue of their ability to elicit an antidepressant response in mammals. Antidepressant activity is determined by the L-5-hydroxytryptophan potentiation assay in rats described in *Brit. J. Pharmacol.*, 20, pp. 106–120 (1963) and *J. Med. Chem.*, 24, 74 (1980); and the tetrabenazine induced ptosis assay in mice, [International Journal of Neuropharmacology, 8, 72 (1969)], standard assays for the determination of antidepressant activity.

In the tetrabenazine induced ptosis assay, male mice (Charles River, CD-1), weighing 20 to 39 g, are used in test groups of five animals. Test compounds are dissolved, or suspended with 1 drop of Tween-80, in distilled water and administered to the animals in volumes of 10 cc per kg of body weight. Tetrabenazine methanesulfonate (76.78% as the free base) is dissolved in distilled water and the concentration of the solution is adjusted so that the dose, administered intraperitoneally (i.p.) to the animals, is 40 mg of tetrabenazine base per kg of animal body weight.

The test compound is administered intraperitoneally (i.p.) or perorally (p.o.) to the subject animals, and the tetrabenazine solution is administered 30 minutes or 60 minutes, respectively, thereafter. Tetrabenazine solution and the solvent used to dissolve or suspend the test compounds are administered by the same route and at the same intervals as the test compounds to a control group.

The subject animals are placed in individual plastic containers (10½″×8″×6″) thirty (i.p.) and sixty minutes (p.o.) after administration of the tetrabenazine solution, and one minute thereafter, the animals are scored for ptosis on the following scale:

| Eye Closure | Score |
|---|---|
| Eyes closed | 4 |
| Eyes ¾ closed | 3 |
| Eyes ½ closed | 2 |
| Eyes ¼ closed | 1 |
| Eyes open | 0 |

The total score for each group of 5 animals will therefore vary from 0 to 20; these scores are used as the indications of the activity of the test compound.

The vehicle-control group score is used as a determination of the validity of each test. The results are discarded and the test is repeated, if the control score is determined to be less than 17.

A dose range determination is generally reserved for those compounds which inhibit ptosis by greater than about 45–50% at the screening dose.

For calculation of the $ED_{50}$ value of a test compound; i.e., the calculated dose at which the test compound effects a 50% inhibition of tetrabenazine-induced ptosis, four or five doses are administered, and only vehicle-control scores of 17 to 20 are acceptable. A linear-regression analysis is used to estimate $ED_{50}$ values and 95% confidence limits.

In the L-5-hydroxytryptophan potentiation assay groups of six male Wistar rats (150–200 grams each) are used. Pargyline hydrochloride is prepared and administered four hours before testing by subcutaneous injection at 75 mg/kg in 1% saline and a dosage volume of 1.0 ml/kg. Thirty minutes before testing, drugs are prepared and dosed using distilled water and, if insoluble, a suitable surfactant is added. Control groups receive vehicle. Drugs are routinely administered intraperitoneally at a dosage volume of 10 ml/kg. L-5-hydroxytryptophan (5-HTP) is prepared at 1.0 mg/kg in distilled water and is administered intraperioneally in volumes proportional to 10 ml/kg. Drugs are administered in a randomized manner and 15 minutes post 5-HTP treatment, the animals are observed for 15 minutes.

A compound is considered to potentiate 5-HTP activity if the animals exhibit continuous forelimb clonus. Potentiation is expressed as normalized percent potentiation relative to vehicle control. $ED_{50}$ values (the calculated dose at which the test compound effects a 50% inhibition of continuous forelimb clonus) and 95% confidence limits are determined by linear analysis.

The antidepressant activity of representative compounds is provided in Table 4.

TABLE 4

| | Antidepressant Activity | |
|---|---|---|
| Compound | 5-HTP $ED_{50}$ mg/kg i.p. | TBZ $ED_{50}$ mg/kg i.p. |
| 1-methyl-4-(2,3,4,5,6-pentafluorophenoxy)-4-phenylpiperidine hydrochloride | 8.1 | 1.3 |
| 4-(2,3,4,5,6-pentafluorophenoxy)-4-phenylpiperidine maleate | 14.5 | 1.0 |
| 4-(4-chlorophenyl)-1-methyl-4-(2,3,4,5,6-pentafluorophenoxy)-piperidine fumarate | 11.9 | 38.9 |
| 4-(4-chlorophenyl)-4-(2,3,4,5,6-pentafluorophenoxy)piperidine fumarate | 37 | 20.0 |
| 4-(4-fluorophenyl)-1-methyl-4-(2,3,4,5,6-pentafluorophenoxy)-piperidine hydrochloride | 7.0 | 5.4 |
| 4-(2-fluorophenyl)-1-methyl-4-(2,3,4,5,6-pentafluorophenoxy)piperidine oxalate | | 3.8 |
| 4-(4-methylphenyl)-1-methyl-4-(2,3,4,5,6-pentafluorophenoxy)-piperidine hydrochloride | | 7.0 |
| 4-(4-fluorophenyl)-4-(2,3,4,5,6-pentafluorophenoxy)piperidine hydrochloride | <10 | 4.8 |
| 4-(4-methylphenyl)-4-(2,3,4,5,6-pentafluorophenoxy)-piperidine maleate | 14.5 | 8.3 |
| 4-(2-fluorophenyl)-4-(2,3,4,5,6-pentafluorophenoxy)-piperidine maleate | <20 | 6.4 |
| 1-methyl-4-(2,3,4,5,6-pentafluorophenoxy)piperidine | 4.7 | 4.7 |
| 1-(dimethylphosphinylmethyl)-4-(2,3,4,5,6-pentafluorophenoxy)-piperidine | 9.1 | |
| amitriptyline | 7.1 | 1.5 |

Antidepressant activity is achieved when the compounds of this invention are administered to a subject requiring such treatment at an effective oral, parental or intravenous dose of from 1 to 100 mg/kg of body weight per day.

It is to be understood that the dosages set forth above with respect to analgesic, anticonvulsant, antidepressant, and antihypertensive activity for any particular subject should be adjusted according to the individual need and the professional judgment of the person administering or supervising the administration of the aforesaid compound. It is further understood that the dosages set forth herein are exemplary only and that they do not, to any extent, limit the scope or practice of the invention.

Effective amounts of the compounds of the present invention may be administered to a subject by any one of various methods, for example, orally as in capsules or tablets, parenterally in the form of sterile solutions or suspensions, and in some cases intravenously in the form of sterile solutions. The compounds of this invention, while effective themselves, may be formulated and administered in the form of their pharmaceutically acceptable acid addition salts for purposes of stability, convenience, increased solubility and the like.

Preferred pharmaceutically acceptable acid addition salts include salts of mineral acids, for example, hydrochloric acid, sulfuric acid, nitric acid and the like, salts of monobasic carboxylic acids such as, for example, carboxysuccinic acid, citric acid and the like.

Effective quantities of the compounds of this invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0 and 300 milligrams of the active compound.

The tablets, pills, capsules, troches and the like may also contain the following ingredients: a binder such as microcrystalline cellulose, gum tragancanth or gelatin; and excipient such as starch or lactose, a disintegrating agent such as alginic acid, Promogel ™, cornstarch and the like; a lubricant such as magnesium stearate or Sterotex; a glidant such as colloidal silicon dioxide; and a sweetening agent such as sucrose or saccharin or a flavoring agent such as peppermint, methyl salicylate, or orange flavoring. When the dosage unit is a capsule, it may contain, in addition to materials of the preceeding type, a liquid carrier such as a fatty oil. Other dosage unit forms may contain other various materials which modify the physical form of the dosage unit such as, for example, coatings. Thus, tablets or pills may be coated with sugar, shellac, or other enteric coating agents. A syrup may contain, in addition to the active compounds, sucrose and/or flavorings. Materials used in preparing these various compositions should be pharmaceutically pure and nontoxic in the amounts used.

For the purpose of parenteral therapeutic administration, the active compounds of this invention may be incorporated into a solution or suspension. These preparations should contain at least 0.1% of active compound, but may be varied between 0.5 and about 50% of the weight thereof. The amount of active compounds in such compositions is such that a suitable dosage will be obtained. Preferred compositions and preparations according to the present invention are prepared so that a parenteral dosage unit contains between 0.5 and 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. The parenteral preparation can be enclosed in ampules, disposable syringes or multiple dose vials made of glass or plastic.

EXAMPLES

The following Examples are for illustrative purposes only and are not to be construed as limiting the invention.

EXAMPLE 1

1-Benzyl-4-(2,3,4,5,6-pentafluorophenoxy)piperidine hydrochloride

A stirred mixture of 10.33 g of 1-benzyl-4-hydroxy piperidine, 9.93 g of pentafluorophenol, and 15.58 g of triphenylphosphine in 200 ml of benzene was cooled to 10° C. At this temperature, a solution of 10.35 g of diethyl azodicarboxylate in 50 ml of benzene was added, dropwise, over one hour. After stirring for 20 hours at ambient temperature, the reaction mixture was filtered and concentrated to an oil. The oil was purified by means of high pressure liquid chromatography (silica gel; elution with ethylacetate/dichloromethane 1:1). Evaporation of the appropriate fractions afforded 14.5 g of 1-benzyl-4-(2,3,4,5,6-pentafluorophenoxy)piperidine as an oil. Conversion of the free base to the corresponding hydrochloride salt afforded 8.2 g (42%) of 1-benzyl-4-(2,3,4,5,6-pentafluorophenoxy)piperidine hydrochloride, m.p. 244°–246° C.

ANALYSIS: Calculated for $C_{18}H_{16}F_5NO \cdot HCl$: 54.89% C, 4.32% H, 3.56% N; Found: 55.33% C, 4.57% H, 3.54% N.

EXAMPLE 2

4-(2,3,4,5,6-Pentafluorophenoxy)piperidine hydrochloride

To 2.0 g of 10% palladium on carbon was added 6.0 g of 1-benzyl-4-(2,3,4,5,6-pentafluorophenoxy)piperidine hydrochloride in 250 ml of methanol. The reaction mixture was pressurized to 50 psi with hydrogen and shaken on a Parr apparatus at room temperature for five hours. The mixture was then filtered and concentrated. Recrystallization of the concentrate from hot isopropanol afforded 1.9 g (42%) of 4-(2,3,4,5,6-pentafluorophenoxy)piperidine hydrochloride, m.p. 187°–190° C.

ANALYSIS: Calculated for $C_{11}H_{10}F_5NO \cdot HCl$: 43.49% C 3.62% H 4.61% N Found: 43.11% C, 3.70% H, 4.54% N.

EXAMPLE 3

1-Methyl-4-(2,3,4,5,6-pentafluorophenoxy)piperidine hydrochloride

To a stirring solution of 5.0 g of 4-(2,3,4,5,6-pentafluorophenoxy)piperidine in 50 ml of methanol was added 15 ml of 37% formaldehyde. After refluxing for 1 hour, the solution was cooled to ice bath temperature, treated (portionwise), with 2.5 g of sodium borohydride, and then stirred at ambient temperature for one hour. Evaporation of the volatiles yielded a residue which was taken up in ethyl acetate, washed with water followed by a saturated sodium chloride solution, and dried over anhydrous magnesium sulfate. Concentration afforded an oil which was purified by means of high pressure liquid chromatography (silica gel; elution with 10% methanol/dichloromethane) to yield 4.2 g of 1-methyl-4-(2,3,4,5,6-pentafluorophenoxy)piperidine as an oil. The oil which was dissolved in isopropanol and acidified to pH 1 with etheral hydrogen chloride to precipitate 2.34 g (39%) of the corresponding hydrochloride salt, m.p. 151°–153° C.

ANALYSIS: Calculated for $C_{12}H_{12}F_5NO \cdot HCl$: 45.35% C, 4.09% H, 4.41% N; Found: 45.09% C, 4.06% H, 4.31% N.

EXAMPLE 4

1-[2-(N,N-Dimethylamino)ethyl]-4-(2,3,4,5,6-pentafluorophenoxy)piperidine dihydrochloride A stirred mixture of 5 g of sodium bicarbonate, 4.44 g of 4-(2,3,4,5,6-pentafluorophenoxy)piperidine, and 40 ml of dimethylformamide was treated, dropwise, with a solution of 2.15 g of 2-dimethylaminoethyl chloride in 20 ml of dimethylformamide. After stirring for five hours at 85° C., the reaction mixture was filtered, and the filtrate poured into water and extracted with ethyl acetate. The organic layer was washed with water followed by a saturated sodium chloride solution and dried over anhydrous magnesium sulfate. After filtering, evaporation of the volatiles afforded an oil which was eluted with 20% methanol/dichloromethane on a silica gel column via flash chromatography. The desired fractions were evaporated to afford 2.58 g of 1-[2-(N,N-dimethylamino)ethyl]-4-(2,3,4,5,6-pentafluorophenoxy)piperidine as an oil. The oil was dissolved in isopropanol and the solution acidified to pH 1 with etheral hydrogen chloride to precipitate 2.05 g (29.3%) of the corresponding dihydrochloride salt, m.p. 276° C. (dec.).

ANALYSIS: Calculated for $C_{15}H_{19}F_5N_2O \cdot 2HCl$: 43.80% C, 5.11% H, 6.81% N; Found: 43.80% C, 5.31% H, 6.77% N.

EXAMPLE 5

1-[3-(N,N-Dimethylamino)propyl]-4-(2,3,4,5,6-pentafluorophenoxy)piperidine dihydrochloride A mixture of 10 g of sodium bicarbonate, 4.0 g of 4-(2,3,4,5,6-pentafluorophenoxy)piperidine, and 50 ml of dimethylformamide was treated, dropwise, with a solution of 2.00 g of dimethylaminopropyl chloride in 20 ml of dimethylformamide. After stirring at 80° C. for eight hours, the reaction mixture was filtered and the filtrate poured into water and extracted with ethyl acetate. The organic layer was washed with water followed by a saturated solution of sodium chloride and dried over anhydrous magnesium sulfate. After filtering, evaporation of the volatiles afforded a residue which was eluted with 20% methanol/dichloromethane on a silica gel column via flash chromatography. The desired fractions were evaporated to afford 2.74 g of 1-[3-(N,N-dimethylamino)propyl]-4-(2,3,4,5,6-pentaflurophenoxy)piperidine as an oil. The oil was dissolved in isopropanol and acidified to pH 1 with etheral hydrogen chloride to precipitate 1.8 g (28%) of 1-[3-dimethylaminopropyl]-4-(2,3,4,5,6-pentaflurophenoxy)piperidine hydrochloride, m.p. 260° C.(dec.).

ANALYSIS: Calculated for $C_{16}H_{21}F_5N_2O \cdot 2HCl$: 45.18% C, 5.41% H, 6.59% N; Found: 44.82% C, 5.39% H, 6.53% N.

EXAMPLE 6

1-{4-[1-[4-(2-Methoxyphenyl)piperazin-1-yl]-2-butynyl]}-4-(2,3,4,5,6-pentafluorophenoxy)piperidine dioxalate A mixture of 100 ml of dioxane, 5.1 g of 4-(2,3,4,5,6-pentafluorophenoxy)-1-propynylpiperidine, 3.8 g of 4-(2-methoxyphenyl)piperazine, of 2.0 g paraformaldehyde, and 0.1 g of copper (I) chloride was stirred at 80° C. for two hours. The reaction mixture was then cooled, diluted with 300 ml ethyl acetate, and filtered. Evaporation of the filtrate afforded a residue which was purified by means of high pressure liquid chromatography (silica gel; elution with ethyl acetate) to yield 5.7 g of 1-{4-[1-[4-(2-methoxyphenyl)piperazin-1-yl]-2-butynyl]}-4-(2,3,4,5,6-pentafluorophenoxy)piperidine as an oil. The oil was dissolved in of 2.2 g in warm ethanol and treated with an ethanolic solution of 1.16 g of oxalic acid followed by 200 ml of diethyl ether to precipitate the corresponding dioxalate salt. Recrystallization from ethanol/diethyl ether to precipitate the corresponding dioxalate salt. Recrystallization from ethanol/diethyl ether (1:2) afforded 2.0 g (66%) of 1-{4-[1-[4-(2-methoxyphenyl)piperazin-1-yl]-2-butynyl]}-4-(2,3,4,5,6-pentafluorophenoxy)piperidine dioxalate, m.p. 123°-125° C.

ANALYSIS: Calculated for $C_{26}H_{28}F_5N_3O_2 \cdot 2(CO_2H)_2$: 52.25% C, 4.68% H, 6.09% N; Found: 51.11% C, 4.70% H, 5.99% N.

EXAMPLE 7

1-{4-[1-[4-(2-Methoxyphenyl)piperazin-1-yl]butyl]}-4-(2,3,4,5,6-pentafluorophenoxy)piperidine dioxalate A suspension of 0.5 g of 10% palladium on carbon in 25 ml ethanol was treated with a solution of 3.4 g of 1-{4-[1-[4-(2-methoxyphenyl)piperazin-1-yl]-2-butynyl]}-4-(2,3,4,5,6-pentafluorophenoxy)piperidine in 175 ml ethanol and then shaken under hydrogen for four hours at ambient temperature. The mixture was filtered through celite, and the filtrate evaporated to afford 3.0 g of 1-{4-[1-[4-(2-methoxyphenyl)piperazin-1-yl]butyl]}-4-(2,3,4,5,6-pentafluorophenoxy)piperidine as an oil. The oil was dissolved in ethanol and treated with a solution of 1.5 g of oxalic acid in 50 ml of ethanol. The resultant precipitate was recrystallized from ethanol to yield 2.3 g (47%) of 1-{4-[1-[4-(2-methoxyphenyl)piperazin-1-yl]butyl]}-4-(2,3,4,5,6-pentafluorophenoxy)piperidine dioxalate, m.p. 138°-140° C.

ANALYSIS: Calculated for $C_{26}H_{32}F_5N_3O_2 \cdot 2(CO_2H)_2$: 51.95% C, 5.23% H, 6.06% N; Found: 51.55% C, 5.35% H, 5.85% N.

EXAMPLE 8

1-[(6-Fluoro-1,2-benzisoxazol-3-yl)propyl]-4-(2,3,4,5,6-pentafluorophenoxy)piperidine hydrochloride A mixture of 10 g of sodium bicarbonate, and 0.10 g of potassium iodide, 4.13 g of 4-(2,3,4,5,6-pentafluorophenoxy)piperidine and 75 ml of dimethylformamide was treated with a solution of 3.41 g of 3-(3-chloropropyl)-6-fluoro-1,2-benzisoxazole in 25 ml dimethylformamide and stirred at 68° C. for 5.5 hours. The mixture was then cooled, poured into water, and then extracted with ethyl acetate. The organic layer was washed with water followed by a saturated sodium chloride solution and dried over anhydrous magnesium sulfate. After filtering, evaporation of the volatiles afforded a residue which was purified by means of high pressure liquid chromatography (silica gel; elution with ethyl acetate) to yield 2.63 g of 1-[-(6-fluoro-1,2-benzisoxazol-3-yl)propyl]-4-(2,3,4,5,6-pentafluorophenoxy)piperidine as an oil. The oil was dissolved in diethyl ether and the solution acidified to pH 1 with etheral hydrogen chloride to precipitate the corresponding hydrochloride salt. Recrystallization from isopropanol afforded 1.80 g (15.4%) of 1-[-(6-fluoro-1,2-benzisoxazol-3-yl)propyl]-4-(2,3,4,5,6-pentafluorophenoxy)piperidine hydrochloride, m.p. 187°-189° C.

ANALYSIS: Calculated for $C_{21}H_{18}F_6N_2O_2 \cdot HCl$: 52.45% C, 3.95% H, 5.83% N; Found: 52.10% C, 3.99% H, 5.71% N.

EXAMPLE 9

1-[1-(1,3-Dihydro-2-oxo-2H-benzimidazol-1-yl)propyl]-4-(2,3,4,5,6-pentafluorophenoxy)piperidine A mixture of 10 g of sodium bicarbonate, 3.58 g of 1-(3-chloropropyl)-1,3-dihydro-2-oxo-2H-benzimidazole and 60 ml of dimethylformamide was treated with a solution of 4.0 g of 4-(2,3,4,5,6-pentafluorophenoxy)piperidine in 20 ml dimethylformamide and stirred at 75° C. for 1.5 hours. The reaction mixture was then cooled and filtered. The filtrate was poured into water and extracted with ethyl acetate. The organic layer was washed with water followed by a saturated sodium chloride solution, and dried over anhydrous magnesium sulfate. After filtering, evaporation of the volatiles afforded a residue which was purified by means of high pressure liquid chromatography (silica gel; elution with 5% methanol/dichloromethane). Recrystallization from isopropyl ether afforded 3.6 g (54%) of 1-[1-(1,3-dihydro-2-oxo-2H-benzimidazol-1-yl)propyl]-4-(2,3,4,5,6-pentafluorophenoxy)piperidine, m.p. 117°-120° C.

ANALYSIS: Calculated for $C_{21}H_{20}F_5N_3O_2$: 57.14% C, 4.54% H, 9.52% N; Found: 57.08% C, 4.53% H, 9.41% N.

EXAMPLE 10

1-[(5,6-Dimethoxy-1,2-benzisoxazol-3-yl)propyl]-4-(2,3,4,5,6-pentafluorophenoxy)piperidine hydrochloride A mixture of 10 g of sodium bicarbonate, 0.12 g of potassium iodide, 5.0 g of 4-(2,3,4,5,6-pentafluorophenoxy)piperidine and 75 ml of dimethylformamide was treated with a solution of 5.37 g of 3-(3-chloropropyl)-5,6-dimethoxy-1,2-benzisoxazole in 25 ml dimethylformamide and stirred for five hours at 70° C. The reaction mixture was filtered and the filtrate poured into water and extracted with ethyl acetate. The organic layer was washed with water followed by a saturated sodium chloride solution, and dried over anhydrous magnesium sulfate. After filtering, evaporation under reduced pressure afforded a residue which was purified by means of high pressure liquid chromatography (silica gel; elution with ethyl acetate) to yield 5.5 g of 1-[(5,6-dimethoxy-1,2-benzisoxazol-3-yl)propyl]-4-(2,3,4,5,6-pentaflurorphenoxy)piperidine as a waxy solid. This material was dissolved in isopropanol and acidified to pH 1 with etheral hydrogen chloride to precipitate the corresponding hydrochloride salt. Recrystallization from isopropanol afforded 3.3 g (36%) of 1-[(5,6-dimethoxy-1,2-benzisoxazol-3-yl)propyl]-4-(2,3,4,5,6-pentafluorophenoxy)piperidine hydrochloride, m.p. 210°-212° C.

ANALYSIS: Calculated for $C_{23}H_{23}F_5N_2O_4 \cdot HCl$: 52.82% C, 4.60% H, 5.36% N; Found: 52.56% C, 4.69% H, 5.20% N.

EXAMPLE 11

1-{3-[4-(2-Methoxyphenyl)piperazin-1-yl]propyl}-4-(2,3,4,5,6-pentafluorophenoxy)piperidine dihydrochloride A mixture of 10 g of potassium carbonate, 0.18 g of potassium iodide, 4.0 g of 4-(2,3,4,5,6-pentafluorophenoxy)piperidine and 50 ml of dimethylformamide was treated with a solution of 4.56 g of 1-(3-chloropropyl)-4-(2-methoxyphenyl)piperazine in 25 ml dimethylformamide and stirred for seven hours at 75° C. After cooling to room temperature, the reaction mixture was poured into water and extracted with ethyl acetate. The organic layer was washed with water followed by a saturated sodium chloride solution and dried over anhydrous magnesium sulfate. After filtering, evaporation afforded a residue which was purified by means of high pressure liquid chromatography (silica gel; elution with 7.5% methanol/dichloromethane). Evaporation of the appropriate fractions afforded 3.84 g of 1-{3-[4-(2-methoxyphenyl)piperazin-1-yl]propyl}-4-(2,3,4,5,6-pentafluorophenoxy)piperidine as an oil. The oil was dissolved in isopropanol and acidified to pH 1 with etheral hydrogen chloride to precipitate the corresponding dihydrochloride salt. Recrystallization from isopropanol afforded 3.34 g (44.6%) of 1-{3-[4-(2-methoxyphenyl)piperazin-1-yl]propyl}-4-(2,3,4,5,6-pentaflurophenoxy)piperidine hydrochloride, m.p. 261°-263° C.

ANALYSIS: Calculated for $C_{25}H_{30}F_5N_3O_2 \cdot 2HCl$: 52.45% C, 5.59% H, 7.34% N; Found: 52.30% C, 5.60% H, 7.26% N.

EXAMPLE 12

1-[4,4-bis-(4-Fluorophenyl)butyl]-4-(2,3,4,5,6-pentafluorophenoxy)piperidine oxalate A stirring mixture of 10 g of sodium bicarbonate in 50 ml dimethylformamide was treated with 4.0 g of 4-(2,3,4,5,6-pentafluorophenoxy)piperidine followed by a solution of 4.06 ml of 4,4-bis-(4-fluorophenyl)butyl chloride in 10 ml of dimethylformamide, and then stirred at 78° C. for 20 hours. After filtering, the filtrate was poured into water and extracted with ethyl acetate. The organic layer was washed with water followed by a saturated sodium chloride solution and dried over anhydrous magnesium sulfate. Filtration followed by evaporation of the volatiles afforded a residue which was purified by means of high pressure liquid chromatography (silica gel; elution with 20% ethyl acetate/dichloromethane) to afford 5.44 g of 1-[4,4-bis-(4-fluorophenyl)butyl]-4-(2,3,4,5,6-pentafluorophenoxy)piperidine as an oil. The oil was dissolved in hot isopropanol and acidified with an etheral solution of oxalic acid to precipitate the corresponding oxalate salt. Recrystallization from isopropanol afforded 2.75 g (30.0%) of 1-[4,4-bis-(4-fluorophenyl)butyl]-4-(2,3,4,5,6-pentafluorophenoxy)piperidine oxalate, m.p. 183°-185° C.

ANALYSIS: Calculated for $C_{27}H_{24}F_7NO \cdot (COOH)_2$: 57.90% C, 4.33% H, 2.33% N; Found: 57.71% C, 4.28% H, 2.30% N.

EXAMPLE 13

1-[(Dimethylphosphinyl)methyl]-4-(2,3,4,5,6-pentafluorophenoxy)piperidine

To a stirring mixture of 9.0 g of potassium carbonate in 100 ml of dimethylformamide was added 8.0 g of 4-(2,3,4,5,6-pentafluorophenoxy)piperidine and 9.5 g of dimethylphosphinylmethyl chloride. After stirring at 80° C. for 30 hours, the reaction mixture was cooled, poured into water, and extracted with ethyl acetate. The organic layer was washed with water followed by a saturated sodium chloride solution and dried over anhydrous magnesium sulfate. After filtering, evaporation afforded a residue which was purified by means of high pressure liquid chromatography (silica gel; elution with 5% methanol/dichloromethane). The desired fractions were evaporated to yield a solid which was sublimed to afford 2.37 g (22.1%) of 1-[(dimethylphosphinyl)methyl]-4-(2,3,4,5,6-pentafluorophenoxy)piperidine, m.p. 120°-123° C.

ANALYSIS: Calculated for $C_{14}H_{17}F_5NO_2P$: 47.06% C, 4.76% H, 3.92% N; Found: 47.15% C, 4.95% H, 3.87% N.

EXAMPLE 14

4-(2,3,4,5,6-Pentafluorophenoxy)-4-phenylpiperidine maleate

To a suspension of sodium hydride (60% in oil, 6.4 g) in 50 ml of dry dimethylformamide was added, over a period of ten minutes, a solution of 25 g of 4-hydroxy-4-phenylpiperidine in 100 ml of dry dimethylformamide. After stirring at 50° C., for thirty minutes, the reaction mixture was cooled to ice bath temperature (5° C.). A solution of 18.6 ml of hexafluorobenzene in 100 ml of dry dimethylformamide was then added over a period of thirty minutes, and the resulting mixture stirred at ambient temperature for twenty hours. The mixture was poured into 500 ml water, stirred for five minutes, and extracted with ethyl acetate. The organic layer was washed with water followed by a saturated sodium chloride solution and dried over anhydrous magnesium sulfate. After filtering, evaporation of the solvents afforded a residue which was purified by means of high pressure liquid chromatography (silica gel; elution with 20% methanol/dichloromethane) to afford 21 g (44%) of 4-(2,3,4,5,6-pentafluorophenoxy)-4-phenylpiperidine as an oil.

A sample of the oil was dissolved in isopropanol, acidified to pH 1 with etheral-maleic acid, and then diluted with diethyl ether. The resultant precipitate was collected and dried, to yield 4-(2,3,4,5,6-pentafluorophenoxy)-4-phenylpiperidine maleate, m.p. 141°–142° C.

ANALYSIS: Calculated for $C_{17}H_{14}F_5NO \cdot C_4H_4O_4$: 54.90% C, 3.95% H, 3.05% N; Found: 55.29% C, 4.11% H, 3.14% N.

EXAMPLE 15

1-Methyl-4-(2,3,4,5,6-pentafluorophenoxy)-4-phenylpiperidine oxalate

To 50 ml of methanol, was added 4.0 g of 4-(2,3,4,5,6-pentafluorophenoxy)-4-phenylpiperidine and 15 ml of a 37% aqueous formaldehyde solution. After stirring at 70° C. for two hours, the mixture was cooled, and treated (portionwise) with 2.5 g of sodium borohydride over a period of five minutes. After stirring at ambient temperature for two hours, the reaction mixture was evaporated to a semi-solid. The semi-solid was stirred with 50 ml water, then extracted with ethyl acetate. The organic layer was washed with water, followed by a saturated sodium chloride solution, and dried over anhydrous magnesium sulfate. After filtering, evaporation of the solvent yielded a residue which was purified by means of a high pressure liquid chromatography (silica gel, elution with 5% methanol/dichloromethane). The desired fractions were combined, then evaporated to afford 1-methyl-4-(2,3,4,5,6-pentafluorophenoxy)-4-phenylpiperidine as an oil. The oil was dissolved in isopropanol, and acidified to pH 1 with etheral-oxalic acid. The resultant precipitate was collected and dried to give 2.5 g (47%), of 1-methyl-4-(2,3,4,5,6-pentafluorophenoxy)-4-phenylpiperidine oxalate, m.p. 152°–154° C. (dec).

ANALYSIS: Calculated for $C_{18}H_{16}F_5NO \cdot C_2H_2O_4$: 53.96% C, 4.05% H, 3.13% N; Found: 53.78% C, 4.17% H, 3.19% N.

EXAMPLE 16

4-(4-Chlorophenyl)-4-(2,3,4,5,6-pentafluorophenoxy)piperidine fumarate

To a stirring suspension of sodium hydride (60% in oil, 1.04 g) in 10 ml of dimethylformamide was added 5.0 g of 4-(4-chorophenyl)-4-hydroxypiperidine. After stirring at 50° C. for 0.5 hours, the reaction mixture was cooled to ice bath temperature, and treated, dropwise, with an solution of 3.00 ml of hexafluorobenzene in 10 of dimethylformamide. The reaction mixture was then stirred at room temperature for 24 hours, poured into water, and extracted with ethyl acetate. The organic layer was washed with water followed by a saturated sodium chloride solution, and dried over anhydrous magnesium sulfate.

After filtering, evaporation of the solvent yielded a residue which was purified by means of high pressure liquid chromatography (silica gel; elution with 10% methanol/dichloromethane) to afford 4-(4-chlorophenyl)-4-(2,3,4,5,6-pentafluorophenoxy)piperidine as an oil. The oil was dissolved in ethanol and acidified with an ethanol solution of fumaric acid. The resulting precipitate was collected to yield 2.15 g (18.15%) of 4-(4-chlorophenyl)-4-(2,3,4,5,6-pentafluorophenoxy)piperidine fumarate, mp 183°–185° C.

ANALYSIS: Calculated for $C_{17}H_{13}F_5NO \cdot C_4H_4O_4$: 51.06% C, 3.44% H, 2.84% N; Found: 51.31% C, 3.38% H, 2.92% N.

EXAMPLE 17

4-(4-Chlorophenyl)-1-methyl-4-(2,3,4,5,6-pentafluorophenoxy)piperidine fumarate

To a stirring solution of 3.9 g of 4-(4-chlorophenyl)-4-(2,3,4,5,6-pentafluorophenoxy)piperidine in 50 ml of methanol was added 13 ml of formaldehyde (37% aqueous solution). After stirring at 65° C. for two hours, the mixture was cooled to ice bath temperature and treated, portionwise, with 2.3 g of sodium borohydride. The reaction mixture was then stirred at room temperature for half an hour. The mixture was evaporated and the residue dissolved in ethyl acetate. The organic layer was washed with water followed by a saturated sodium chloride solution, and dried over anhydrous magnesium sulfate.

After filtering, evaporation of the solvents yielded a residue which was purified by means of high pressure liquid chromatography (silica gel, elution with ethyl acetate). The desired fractions were evaporated to yield 2.4 g of 4-(4-chlorophenyl)-1-methyl-4-(2,3,4,5,6-pentafluorophenoxy)piperidine as an oil. The oil was dissolved in diethyl ether and acidified with an etheral solution of fumaric acid. The resulting precipitate was collected to afford solid 2.0 g (39.41%) of 4-(4-chlorophenyl)-1-methyl-4-(2,3,4,5,6-pentafluorophenoxy)piperidine fumarate, m.p. 171°–173° C.

ANALYSIS: Calculated for $C_{18}H_{15}ClF_5NO \cdot C_4H_4O_4$: 52.02% C, 3.74% H, 2.76% N; Found: 51.93% C, 3.52% H, 3.02% N.

EXAMPLE 18

4-(4-Fluorophenyl)-1-methyl-4-(2,3,4,5,6-pentafluorophenoxy)piperidine hydrochloride To a suspension of sodium hydride (60% in oil, 3.8 g) in 20 ml of dimethylformamide was added a solution of 15 g of 4-(4-fluorophenyl)-4-hydroxy-1-methylpiperidine in 100 ml of dimethylformamide. After stirring at 70°–80° C. for fifteen minutes, the reaction mixture was cooled with an ice-bath, and treated with a solution of 11.6 ml of hexafluorobenzene in 15 ml of dimethylformamide over a period of thirty minutes. After stirring at ambient temperature for twenty hours, the mixture was poured into 400 ml of water, stirred for five minutes, and extracted with ethyl acetate (3×). The organic layer was washed with water, followed by a saturated solution of sodium chloride, and dried over anhydrous magnesium sulfate.

After filtering, evaporation of the solvent afforded a residue which was purified by means of high pressure liquid chromatography (silica gel, elution with 10% methanol/dichloromethane) to yield 12.4 g (46%) of 4-(4-fluorophenyl)-1-methyl-4-(2,3,4,5,6-pentafluorophenoxy)piperidine as an oil.

A sample of this oil (2.6 g) was dissolved in 25 ml ethanol, the pH was adjusted to 1 with etheral-hydrogen chloride, and the solution diluted with 200 ml of diethyl ether. The resultant precipitate was collected and dried to give 2.6 g, of 4-(4-fluorophenyl)-1-methyl-4-(2,3,4,5,6-pentafluorophenoxy)piperidine hydrochoride, m.p. 170°–172° C.

ANALYSIS: Calculated for $C_{18}H_{15}F_6NO \cdot HCl$: 52.50% C, 3.92% H, 3.40% N; Found: 52.60% C, 4.04% H, 3.49% N.

EXAMPLE 19

4-(4-Fluorophenyl)-4-(2,3,4,5,6-pentafluorophenoxy)piperidine hydrochloride

To a cold solution of 5.0 g of 4-(4-fluorophenyl)-1-methyl-4-(2,3,4,5,6-pentafluorophenoxy)piperidine and 1 ml of triethylamine in 30 ml of dichloromethane, was added a solution of 1.6 ml of α-chloroethylchloroformate in 10 ml of dichloromethane. After stirring at ambient temperature for twenty hours, the mixture was washed with water, followed by a saturated solution of sodium chloride, and dried over anhydrous magnesium sulfate. After filtering, evaporation of the solvent afforded a residue which was purified by means of high pressure liquid chromatography (silica gel; elution with dichloromethane). Evaporation of the desired fractions afforded 4.0 g (65%) of 1-(1-chloroethoxycarbonyl)-4-(4-fluorophenyl)-1-(2,3,4,5,6-pentafluorophenoxy)piperidine as an oil.

A 4.0 g aliquot of the oil was dissolved in 50 ml methanol; stirred at reflux (70° C.) for two hours; cooled then evaporated to a glassy solid, which was recrystallized from methanol/diethyl ether (1:50) to afforded 2.4 g (71%) of 4-(4-fluorophenyl)-4-(2,3,4,5,6-pentafluorophenoxy)piperidine hydrochloride, m.p. 179°–180° C.

ANALYSIS: Calculated for $C_{17}H_{13}F_6NO \cdot HCl$: 51.33% C, 3.55% H, 3.52% N; Found: 51.20% C, 3.48% H, 3.33% N.

EXAMPLE 20

(4-(4-Methylphenyl)-1-methyl-4-(2,3,4,5,6-pentafluorophenoxy)piperidine hydrochloride To a suspension of sodium hydride (2.2 g, 60% in oil) in 20 ml of dimethylformamide, was added a solution of 11.0 g of 4-hydroxy-4-(4-methylphenyl)-1-methylpiperidine in 50 ml of dimethylformamide. After heating to 85° C. for thirty minutes, the mixture was cooled with an ice-bath, and treated over a period of ten minutes with a solution of 7 ml of hexafluorobenzene in 20 ml of dimethylformamide. After stirring at ambient temperature for twenty hours, the mixture was poured into 200 ml water, stirred for five minutes, then extracted with ethyl acetate (2×). The organic layer was washed with water (2×), followed by a saturated solution of sodium chloride, and dried over anhydrous magnesium sulfate. After filtering, evaporation of the solvent afforded a residue which was purified by means of high pressure liquid chromatography (silica gel; elution with 10% methanol/dichloromethane). The desired fractions were combined, and evaporated to yield 13 g of (4-(4-methylphenyl)-1-methyl-4-(2,3,4,5,6-pentafluorophenoxy)piperidine as an oil.

A 3.0 g alliquot of the oil was dissolved in 50 ml ethanol, acidified to a pH 1 with etheral hydrogen chloride, and diluted with 200 ml of diethyl ether. The resultant precipitate was collected and dried to give 3.2 g (65%) of (4-(4-methylphenyl)-1-methyl-4-(2,3,4,5,6-pentafluorophenoxy)piperidine hydrochloride, m.p. 158°–160° C.

ANALYSIS: Calculated for $C_{19}H_{18}F_5NO \cdot HCl$: 55.95% C, 4.70% H, 3.44% N; Found: 56.18% C, 4.82% H, 3.59% N.

EXAMPLE 21

4-(4-Methylphenyl)-4-(2,3,4,5,6-pentafluorophenoxy)piperidine maleate

To a cold solution of 7.5 g of 4-(4-methylphenyl)-1-methyl-4-(2,3,4,5,6-pentafluorophenoxy)piperidine and 2.9 ml of triethylamine in 50 ml dichloroethane was added a solution of 2.4 ml of α-chloroethylchloroformate in 20 of dichloroethane. After stirring at 80° C. for two hours, the mixture was cooled; washed with water, followed by a saturated solution of sodium chloride, and then dried over anhydrous magnesium sulfate. After filtering, evaporation of the solvent afforded a residue which was purified by means of high pressure liquid chromatography (silica gel; elution with dichloromethane) to yield 5.0 g (54%) of the intermediate carbamate as an oil.

The oil was dissolved in 50 ml methanol, stirred at reflux for two hours, then evaporated to a semi-solid. The semi-solid was dissolved in 20 ml water, adjusted to pH 10 by the addition of aqueous sodium carbonate, and extracted with ethyl acetate (2×). The organic layer was washed with water, followed by a saturated sodium chloride solution, and dried over anhydrous magnesium sulfate.

After filtering, evaporation of the solvent afforded 2.7 g of 4-(4-methylphenyl)-4-(2,3,4,5,6-pentafluorophenoxy)piperidine as an oil. The oil was dissolved in 20 ml ethanol, treated with an ethanolic solution of maleic acid (0.9 g), and diluted with 300 ml of diethyl ether. The resultant precipitate was collected and dried to give 2.3 g (44%) of 4-(4-methylphenyl)-4-(2,3,4,5,6-pentafluorophenoxy)piperidine, m.p. 139°–140° C.

ANALYSIS: Calculated for $C_{18}H_{16}F_5NO \cdot C_4H_4O_4$: 55.81% C, 4.26% H, 2.96% N; Found: 56.06% C, 4.52% H, 3.29% N.

EXAMPLE 22

4-(2-Fluorophenyl)-1-methyl-4-(2,3,4,5,6-pentafluorophenoxy)piperidine oxalate

To a suspension of sodium hydride (5.2 g, 60% in oil) in 20 ml of dimethylformamide, was added a solution of 2.0 g of 4-(2-fluorophenyl)-4-hydroxy-1-methylpiperidine in 100 ml of dimethylformamide. After stirring at 80° C. for thirty minutes the mixture was cooled to 10° C., and treated over a period of 30 minutes with 15 ml of hexafluorobenzene in 50 ml of dimethylformamide. After stirring at ambient temperature for twenty hours, the mixture was poured into 300 ml of water, stirred for five minutes; then extracted with ethyl acetate (3×). The organic layer was washed with water (2×), followed by a saturated sodium chloride solution and dried over anhydrous magnesium sulfate.

After filtering, evaporation of the solvents afforded a residue which was purified by means of high pressure liquid chromatography (silica gel; elution with 5% methanol/dichloromethane). The desired fractions were combined and evaporated to afford 8.5 g (23%) of 4-(2-fluorophenyl)-1-methyl-4-(2,3,4,5,6-pentafluorophenoxy)piperidine as an oil.

A portion of this oil (4.0 g) was dissolved in 50 ml of warm ethanol, and treated with an ethanolic solution of oxalic acid (0.96 g). The resultant precipitate was recrystallized from ethanol/diethyl ether (1:5) to afford 2.4 g (11%) of 4-(2-fluorophenyl)-1-methyl-4-(2,3,4,5,6-pentafluorophenoxy)piperidine oxalate, m.p. 170°–171° C. (dec).

ANALYSIS: Calculated for $C_{18}H_{15}F_6NO\cdot(CO_2H)_2$: 51.62% C, 3.68% H, 3.01% N; Found: 51.29% C, 3.85% H, 3.29% N.

EXAMPLE 23

4-(2-Fluorophenyl)-4-(2,3,4,5,6-pentafluorophenoxy)-piperidine maleate

To a cold solution of 15.3 g of 4-(2-fluorophenyl)-1-methyl-4-(2,3,4,5,6-pentafluorophenoxy)piperidine and 3 ml of triethylamine in 75 ml of dichloromethane, was added a solution of 6.1 ml of α-chloroethyl chloroformate in 25 ml dichloromethane. After stirring at ambient temperature for five hours, the mixture was diluted with 200 ml ethyl acetate and 100 ml of diethyl ether. The organic solution was washed with water, followed by a saturated solution of sodium chloride and then dried over anhydrous magnesium sulfate. Filtration followed by evaporation of the solvents afforded 20 g of the intermediate carbamate as an oil.

The carbamate intermediate was dissolved in 70 ml methanol, stirred to 70° C. for two hours, and evaporated. The resultant oil was dissolved in water, adjusted to pH 10 by the addition of aqueous sodium carbonate, and extracted with ethyl acetate. The organic layer was washed with water, followed by a saturated sodium chloride solution, and dried over anhydrous magnesium sulfate. After filtering, evaporation of the solvent afforded 14.4 g (97%) of 4-(2-fluorophenyl)-4-(2,3,4,5,6-pentafluorophenoxy)piperidine as an oil. A 3.0 g sample of the oil was dissolved in 25 ml of ethanol, and treated with a warm ethanolic solution of maleic acid (0.9 g). Dilution with 200 ml of diethyl ether, precipitated the corresponding maleatesalt. Recrystallization from methanol/diethyl ether (1:20) afforded 2.4 g (62%) of 4-(2-fluorophenyl)-4-(2,3,4,5,6-pentafluorophenoxy)piperidine maleate, m.p. 154°–155° C. dec.

ANALYSIS: Calculated for $C_{17}H_{13}F_6NO\cdot C_4H_4P_4$: 52.83% C, 3.59% H, 2.93% N; Found: 52.35% C, 3.60% H, 3.07% N.

EXAMPLE 24

1-Methyl-4-(2,3,4,5,6-pentafluorophenoxy)-4-(4-trifluoromethylphenyl)piperidine

A suspension of sodium hydride (60% in oil, 0.5 g) in 20 ml of dimethylformamide treated with 2.0 g of 1-methyl-4-hydroxy-4-(4-trifluoromethylphenyl)piperidine and then stirred at 60° C. for 20 minutes. The reaction mixture was then cooled to ice bath temperature and treated, dropwise, with a solution of 1.04 ml of hexafluorobenzene in 10 ml of dimethylformamide. After stirring at room temperature for 30 hours, the mixture was poured into water and extracted with ethyl acetate. The organic layer was washed with water followed by a saturated solution of sodium chloride, and dried over anhydrous magnesium sulfate.

After filtering, evaporation of the solvent yielded an oil which was eluted with ethyl acetate on a silica gel column via flash chromatography. The desired fractions were evaporated to an oil which solidified upon standing to afford 2.08 g (61.18%) of 1-methyl-4-(2,3,4,5,6-pentafluorophenoxy)-4-(4-trifluoromethylphenyl)piperidine, m.p. 45°–48° C.

ANALYSIS: Calculated for $C_{19}H_{15}F_8NO$: 53.65% C, 3.53% H, 3.29% N; Found: 53.75% C, 3.27% H, 3.38% N.

EXAMPLE 25

4-(4-Methoxyphenyl)-1-methyl-4-(2,3,4,5,6-pentafluorophenoxy)piperidine hydrochloride To a suspension of sodium hydride (1.2 g, 60% in oil) in 10 ml of dimethylformamide, was added a solution of 6.0 g of 4-hydroxy-4-(4-methoxyphenyl)-1-methylpiperidine in 50 ml of dimethylformamide. After heating at 90° C. for one hour, the mixture was cooled with an ice-bath and treated with a solution of 3.2 ml of hexafluorobenzene in 10 ml of dimethylformamide. After stirring at ambient temperature for twenty hours, the mixture was poured into 200 ml water, stirred for five minutes, then extracted with ethyl acetate (2×). The organic layer was washed with water, followed by a saturated sodium chloride solution and dried over anhydrous magnesium sulfate.

After, filtering, evaporation of the solvents afforded a residue which was purified by means of high pressure liquid chromatography (silica gel; elution with 10% methanol/dichloromethane). The desired fractions were combined, and evaporated to yield 4 g of 4-(4-methoxyphenyl)-1-methyl-4-(2,3,4,5,6-pentafluorophenoxy)piperidine, mp 70°–80° C.

This solid was dissolved in ether and the pH adjusted to 1 with etheral-hydrogen chloride. Recrystallization of the resultant precipitate from ethanol/diethyl ether (1:4) afforded 2.3 g (22%) of 4-(4-methoxyphenyl)-1-methyl-4-(2,3,4,5,6-pentafluorophenoxy)piperidine hydrochloride, m.p. 157°–158° C. (dec).

ANALYSIS: Calculated for $C_{19}H_{18}F_5NO_2\cdot HCl$: 53.84% C, 4.52% H, 3.31% N; Found: 54.32% C, 4.74% H, 3.49% N.

EXAMPLE 26

1-Benzyl-4-(2,3,4,5,6-pentafluorophenoxy)-4-phenyl piperidine

To a stirred suspension of sodium hydride (60% in oil, 4.0 g) in 75 ml of dimethylformamide was added a solution of 22.69 g of 1-benzyl-4-hydroxy-4-phenyl piperidine in 100 ml of dimethylformamide. The mixture was heated with a heat gun to initiate evolution of gas. When evolution had ceased, the mixture was cooled to ice bath temperature and 18.61 g of hexafluorobenzene was added, dropwise, and the reaction was allowed to proceed for 20 hours. The reaction mixture was then poured into 500 ml of iced water and the aqueous suspension extracted with ethyl acetate. The organic layer was washed with water, followed by a saturated sodium chloride solution, and dried over anhydrous magnesium sulfate.

After filtering, evaporation of the solvent afforded a residue which was purified by means of high pressure liquid chromatography (silica gel; elution with 10% ethyl acetate/dichloromethane) to yield 5.36 g, (14.53%) of 1-benzyl-4-(2,3,4,5,6-pentafluorophenoxy)-4-phenyl piperidine, m.p. 80°–83° C.

ANALYSIS: Calculated for $C_{24}H_{20}F_5NO$: 66.53% C, 4.62% H, 3.23% N; Found: 66.53% C, 4.64% H, 3.18% N.

EXAMPLE 27

1-Cyano-4-(2,3,4,5,6-pentafluorophenoxy)-4-phenyl piperidine

A mixture of 15 g of potassium carbonate in 100 ml of chloroform was treated with a solution of 3.22 g of cyanogen bromide in 50 ml of chloroform and heated to reflux (80° C.). A solution of 10.10 g of 1-benzyl-4-(2,3,4,5,6-pentafluorophenoxy)-4-phenyl piperidine in chloroform in 100 ml was then added, dropwise, and the reaction was allowed to continue at reflux for five hours.

After filtering the organic layer was washed with water, followed by a saturated solution of sodium chloride, and dried over anhydrous magnesium sulfate. The solvents were evaporated under reduced pressure to afford an oil which was dissolved in 100 ml of methanol, stirred in the presence of activated charcoal, and filtered. Concentration of the filtrate yielded 8.0 g (94.5% of 1-cyano-4-(2,3,4,5,6-pentafluorophenoxy)-4-phenyl piperidine m.p. 117°–120° C.

ANALYSIS: Calculated for $C_{18}H_{13}F_5N_2O$: 58.70% C, 3.53% H, 7.61% N; Found: 58.96% C, 3.62% H, 7.46% N.

What is claimed is:

1. A compound of the formula

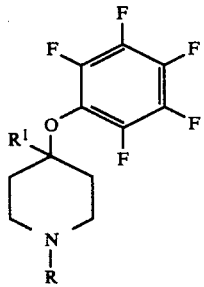

wherein $R^1$ is hydrogen or aryl; and R is a monovalent radical selected from the group consisting of hydrogen, cyano, loweralkyl, arylloweralkyl, bis-arylloweralkyl, aminoloweralkyl, (loweralkylamino)loweralkyl, (diloweralkylamino) loweralkyl, (diloweralkylphosphinyl) loweralkyl, the term aryl in each occurrence

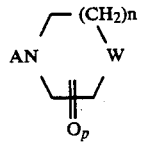

signifying a phenyl group optionally substituted by one or more substituents selected from the group consisting of halogen, loweralkyl, loweralkoxy and trifluoromethyl.

2. A compound as defined in claim 1 wherein $R^1$ is hydrogen.

3. A compound as defined in claim 2 wherein R is hydrogen, loweralkyl, arylloweralkyl or bis-arylloweralkyl.

4. The compound of claim 3 which is 4-(2,3,4,5,6-pentafluorophenoxy)piperidine.

5. The compound of claim 3 which is 1-methyl-4-(2,3,4,5,6-pentafluorophenoxy)piperidine.

6. The compound of claim 3 which is 1-benzyl-4-(2,3,4,5,6-pentafluorophenoxy)piperidine.

7. The compound of claim 3 which is 1-[4,4-bis-(4-fluorophenyl)butyl]-4-(2,3,4,5,6-pentafluorophenoxy)-piperidine.

8. A compound as defined in claim 2 wherein R is cyano.

9. A compound as defined in claim 2 wherein R is aminoloweralkyl, (loweralkylamino)loweralkyl, or (diloweralkylamino)loweralkyl.

10. The compound of claim 9 which is 1-[2-(N,N-dimethylamino)ethyl]-4-(2,3,4,5,6-pentafluorophenoxy)piperidine.

11. The compound of claim 9 which is 1-[3-(N,N-dimethylamino)propyl]-4-(2,3,4,5,6-pentafluorophenoxy)piperidine.

12. A compound as defined in claim 2 wherein R is (diloweralkylphosphinyl)loweralkyl.

13. The compound of claim 12 which is 1-[(dimethylphosphinyl)methyl]-4-(2,3,4,5,6-pentafluorophenoxy)-piperidine.

14. A compound as defined in claim 1 wherein $R^1$ is aryl.

15. A compound as defined in claim 14 wherein $R^1$ is

wherein X is halogen, loweralkyl, loweralkoxy or trifluoromethyl and y is an integer having a value of zero or 1.

16. A compound as defined in claim 15 wherein R is hydrogen, loweralkyl, arylloweralkyl, or bis-arylloweralkyl.

17. The compound of claim 16 which is 4-(2,3,4,5,6-pentafluorophenoxy)-4-phenylpiperidine.

18. The compound of claim 16 which is 1-methyl-4-(2,3,4,5,6-pentafluorophenoxy)-4-phenylpiperidine.

19. The compound of claim 16 which is 4-(4-chlorophenyl)-4-(2,3,4,5,6-pentafluorophenoxy)piperidine.

20. The compound of claim 16 which is 4-(4-chlorophenyl)-1-methyl-4-(2,3,4,5,6-pentafluorophenoxy)-piperidine.

21. The compound of claim 16 which is 4-(4-fluorophenyl)-1-methyl-4-(2,3,4,5,6-pentafluorophenoxy)-piperidine.

22. The compound of claim 16 which is 4-(4-fluorophenyl)-4-(2,3,4,5,6-pentafluorophenoxy)piperidine.

23. The compound of claim 16 which is 4-(4-methylphenyl)-1-methyl-4-(2,3,4,5,6-pentafluorophenoxy)-piperidine.

24. The compound of claim 16 which is 4-(4-methylphenyl)-4-(2,3,4,5,6-pentafluorophenoxy)piperidine.

25. The compound of claim 16 which is 4-(2-fluorophenyl)-1-methyl-4-(2,3,4,5,6-pentafluorophenoxy)-piperidine.

26. The compound of claim 16 which is 4-(2-fluorophenyl)-4-(2,3,4,5,6-pentafluorophenoxy)piperidine.

27. The compound of claim 16 which is 1-methyl-4-(2,3,4,5,6-pentafluorophenoxy)-4-(4-trifluoromethylphenyl)piperidine.

28. The compound of claim 16 which is 4-(4-methoxyphenyl)-1-methyl-4-(2,3,4,5,6-pentafluorophenoxy)-piperidine.

29. The compound of claim 16 which is 1-benzyl-4-(2,3,4,5,6-pentafluorophenoxy)-4-phenyl piperidine.

30. A compound as defined in claim 15 where R is cyano.

31. The compound of claim 30 which is 1-cyano-4-(2,3,4,5,6-pentafluorophenoxy)-4-phenyl piperidine.

32. A compound as defined in claim 15 wherein R is aminoloweralkyl, (loweralkylamino)loweralkyl, or (diloweralkylamino)loweralkyl.

33. A compound as defined in claim 15 wherein R is (diloweralkylphosphinyl)loweralkyl.

34. A convulsion treating composition comprising an inert convulsion-treating adjunct and, as the active ingredient, an effective anticonvulsant amount of a compound as defined in claim 1.

35. A method of treatment which comprises administering to a mammal in need of relief from convulsions a pharmaceutically effective amount of a compound as defined in claim 1.

36. A depression treating composition comprising an inert depression-treating adjunct and, as the active ingredient, an effective antidepressant amount of a compound as defined in claim 1.

37. A method of treatment which comprises administering to a mammal in need of relief from depression a pharmaceutically effective amount of a compound as defined in claim 1.

38. An antihypertensive composition comprising an effective blood pressure lowering amount of the compound as defined in claim 1 and a pharmaceutically acceptable carrier therefor.

39. A method of treating a patient in need of relief from high blood pressure which comprises administering to the patient an effective amount of the compound as defined in claim 1.

40. A pain alleviating composition comprising an inert pain-alleviating adjunct and, as the active ingredient, an amount effective in alleviating pain of a compound as defined in claim 1.

41. A method of alleviating pain comprising administering to a mammal in need of pain alleviation a pain alleviating effective amount of a compound as defined in claim 1.

* * * * *